(12) United States Patent
Kauffman et al.

(10) Patent No.: US 9,364,815 B2
(45) Date of Patent: Jun. 14, 2016

(54) METHOD OF PREPARING AN ALUMINA CATALYST SUPPORT AND CATALYST FOR DEHYDROGENATION REACTIONS, AND ITS USE

(71) Applicant: Saudi Basic Industries Corporation, Riyadh (SA)

(72) Inventors: James W. Kauffman, Katy, TX (US); Patricia A. Hooks, Houston, TX (US); Balamurali Krishna R. Nair, Sugar Land, TX (US)

(73) Assignee: SAUDI BASIC INDUSTRIES CORPORATION, Riyadh (SA)

( * ) Notice: Subject to any disclaimer, the term of this patent is extended or adjusted under 35 U.S.C. 154(b) by 182 days.

(21) Appl. No.: 14/074,101

(22) Filed: Nov. 7, 2013

(65) Prior Publication Data
US 2015/0126792 A1   May 7, 2015

(51) Int. Cl.
*B01J 23/60*   (2006.01)
*B01J 23/63*   (2006.01)
(Continued)

(52) U.S. Cl.
CPC  *B01J 21/04* (2013.01); *B01J 23/58* (2013.01); *B01J 23/62* (2013.01); *B01J 27/10* (2013.01);
(Continued)

(58) Field of Classification Search
CPC ............ B01J 21/04; B01J 23/60; B01J 23/62; B01J 23/624; B01J 23/626; B01J 23/63; B01J 23/6562; B01J 23/78; B01J 23/80; B01J 23/825; B01J 23/83; B01J 23/835; B01J 23/8906; B01J 23/8913; B01J 23/892; B01J 23/8926; B01J 23/8933; B01J 23/894; B01J 23/8946; B01J 23/8953; B01J 23/896; B01J 23/8966; B01J 23/88986; B01J 35/1061; B01J 35/1071; B01J 35/1076; B01J 37/0009; B01J 37/06; B01J 37/12

USPC ......... 502/226–227, 231, 324, 326–328, 330, 502/352, 355; 423/629
See application file for complete search history.

(56) References Cited

U.S. PATENT DOCUMENTS 2,743,215 A * 4/1956 Riblett et al. ................ 208/138
3,392,125 A * 7/1968 Kelly et al. .................. 502/324
(Continued)

FOREIGN PATENT DOCUMENTS

CN   101612583 A   12/2009
CN   101773850 A    7/2010
(Continued)

OTHER PUBLICATIONS

International Search Report of the International Searching Authority for PCT/US2014/064307 (KS20063PCT) mailed Feb. 16, 2015, 6 pages.
(Continued)

*Primary Examiner* — Patricia L Hailey
(74) *Attorney, Agent, or Firm* — Cantor Colburn LLP (57) ABSTRACT

A method of forming a dehydrogenation catalyst support is carried out by forming a mixture comprising a bayerite aluminum hydroxide ($Al(OH)_3$) and water into a support material. The support material is particulized. The particulized support material is compressed to a pressure of at least 5,000 psig to form a shaped body. The shaped body is calcined in pure steam at a temperature of at least 750° C. for at least 0.25 hours to form a catalyst support having an average pore diameter of 200 Å or greater. The catalyst support can then be treated with a dehydrogenation catalyst component so that the catalyst support contains the dehydrogenation catalyst component to form a dehydrogenation catalyst that can then be used by contacting a hydrocarbon feed with the catalyst within a reactor in the presence of steam under dehydrogenation reaction conditions suitable to form dehydrogenated hydrocarbon products.

18 Claims, 3 Drawing Sheets

(51) Int. Cl.

| | | |
|---|---|---|
| *B01J 23/78* | (2006.01) | |
| *B01J 23/80* | (2006.01) | |
| *B01J 23/83* | (2006.01) | |
| *B01J 21/04* | (2006.01) | |
| *C07C 5/32* | (2006.01) | |
| *B01J 27/185* | (2006.01) | |
| *B01J 37/08* | (2006.01) | |
| *B01J 37/10* | (2006.01) | |
| *B01J 23/58* | (2006.01) | |
| *B01J 23/62* | (2006.01) | |
| *B01J 27/10* | (2006.01) | |
| *B01J 35/10* | (2006.01) | |
| *B01J 37/00* | (2006.01) | |
| *C07C 5/333* | (2006.01) | |

(52) U.S. Cl.
CPC .......... *B01J 27/1856* (2013.01); *B01J 35/1014* (2013.01); *B01J 35/1019* (2013.01); *B01J 35/1038* (2013.01); *B01J 35/1042* (2013.01); *B01J 35/1061* (2013.01); *B01J 35/1066* (2013.01); *B01J 35/1071* (2013.01); *B01J 35/1076* (2013.01); *B01J 37/0009* (2013.01); *B01J 37/08* (2013.01); *B01J 37/10* (2013.01); *C07C 5/322* (2013.01); *C07C 5/3337* (2013.01); *C07C 2521/04* (2013.01); *C07C 2523/02* (2013.01); *C07C 2523/14* (2013.01); *C07C 2523/42* (2013.01); *C07C 2523/755* (2013.01); *C07C 2523/89* (2013.01); *C07C 2527/10* (2013.01); *C07C 2527/14* (2013.01)

(56) References Cited

U.S. PATENT DOCUMENTS

| | | | |
|---|---|---|---|
| 4,123,391 A * | 10/1978 | Noguchi et al. | 502/207 |
| 4,200,552 A * | 4/1980 | Noguchi et al. | 502/263 |
| 4,353,815 A | 10/1982 | Antos | |
| 4,401,557 A | 8/1983 | Juguin et al. | |
| 4,547,618 A | 10/1985 | Forbus | |
| 5,358,920 A | 10/1994 | Ma et al. | |
| 6,187,984 B1 | 2/2001 | Wu et al. | |
| 6,414,209 B1 | 7/2002 | Herskowitz et al. | |
| 6,417,422 B1 | 7/2002 | Liu | |
| 6,635,598 B2 | 10/2003 | Dongara et al. | |
| 6,756,340 B2 | 6/2004 | Voskoboynikov et al. | |
| 7,060,864 B2 | 6/2006 | Ghosh et al. | |
| 7,084,318 B2 | 8/2006 | Ghosh et al. | |
| 7,105,713 B2 | 9/2006 | Ghosh et al. | |
| 7,196,237 B2 | 3/2007 | Ghosh et al. | |
| 7,220,700 B2 | 5/2007 | Lowe et al. | |
| 7,244,869 B2 | 7/2007 | Ghosh et al. | |
| 7,279,608 B2 | 10/2007 | Ghosh et al. | |
| 7,285,511 B2 | 10/2007 | Ghosh et al. | |
| 7,294,328 B2 * | 11/2007 | Kawazu et al. | 423/628 |
| 7,304,194 B2 | 12/2007 | Ghosh et al. | |
| 7,341,976 B2 * | 3/2008 | Espinoza et al. | 502/327 |
| 7,368,410 B2 | 5/2008 | Ghosh et al. | |
| 7,399,727 B2 | 7/2008 | Ghosh et al. | |
| 7,446,069 B2 | 11/2008 | Ghosh et al. | |
| 7,507,685 B2 | 3/2009 | Ghosh et al. | |
| 7,560,608 B2 | 7/2009 | Ghosh et al. | |
| 7,576,026 B2 | 8/2009 | Ghosh et al. | |
| 7,579,511 B1 | 8/2009 | Dakka et al. | |
| 7,629,498 B2 | 12/2009 | Brown et al. | |
| 7,635,793 B2 | 12/2009 | Ghosh et al. | |
| 7,662,737 B2 | 2/2010 | Ghosh et al. | |
| 7,674,942 B2 | 3/2010 | Ghosh et al. | |
| 7,713,898 B2 | 5/2010 | Ghosh et al. | |
| 7,972,569 B2 | 7/2011 | Elam et al. | |
| 8,062,987 B2 | 11/2011 | Ghosh et al. | |
| 8,105,971 B2 | 1/2012 | Gaffney et al. | |
| 8,115,041 B2 | 2/2012 | Ghosh et al. | |
| 2001/0008623 A1 | 7/2001 | Kishimoto et al. | |
| 2001/0049461 A1 | 12/2001 | Kishimoto et al. | |
| 2002/0077518 A1 | 6/2002 | Kishimoto | |
| 2004/0162453 A1 | 8/2004 | Kishimoto et al. | |
| 2004/0167013 A1 * | 8/2004 | Ou et al. | 502/64 |
| 2004/0259727 A1 | 12/2004 | Bartolini et al. | |
| 2005/0075273 A1 | 4/2005 | Rabinowitz et al. | |
| 2011/0263416 A1 | 10/2011 | Choi et al. | |
| 2013/0217568 A1 * | 8/2013 | Hazin et al. | 502/226 |
| 2014/0200384 A1 | 7/2014 | Kauffman et al. | |
| 2015/0151283 A1 * | 6/2015 | Kauffman et al. | 502/300 |

FOREIGN PATENT DOCUMENTS

| | | |
|---|---|---|
| CN | 101884922 A | 11/2010 |
| CN | 101940922 A | 1/2011 |
| DE | 19807269 A1 | 8/1999 |
| EP | 0186399 A2 | 7/1986 |
| EP | 749779 A1 | 12/1996 |
| EP | 1243332 A1 | 9/2002 |
| GB | 1289354 A | 9/1972 |
| JP | 2005052730 A | 3/2005 |
| KR | 1020120077688 A1 | 7/2012 |
| WO | 9824742 A1 | 6/1998 |
| WO | 2005051527 A2 | 6/2005 |

OTHER PUBLICATIONS

Written Opinion of the International Searching Authority for PCT/US2014/064307 (KS20063US) mailed Feb. 16, 2015, 6 pages.
Korean Publication No. 1020120077688 (A1); Publication Date: Jul. 10, 2012; Machine Translation; 13 Pages.

* cited by examiner

METHOD OF PREPARING AN ALUMINA CATALYST SUPPORT AND CATALYST FOR DEHYDROGENATION REACTIONS, AND ITS USE

FIELD OF THE INVENTION

The present invention relates to catalysts, their preparation and use, and particularly to those catalysts useful in the conversion of hydrocarbons by dehydrogenation.

BACKGROUND

Dehydrogenation reactions are endothermic reactions and require the input of heat to carry the reaction. At higher temperatures, higher conversion can be achieved. Thus, higher temperatures are often desirable. At higher temperatures, however, coking of the catalyst increases. In the dehydrogenation of hydrocarbons, such as the dehydrogenation of propane to propylene, platinum is generally used for the active catalyst component for steam-based dehydrogenation reactions. In such reactions, the primary cause of catalyst deactivation is due to the buildup of coke on the catalyst and catalyst support surface. The buildup of coke results in thermal decomposition of the alkane/alkene and eventually inhibits the dehydrogenation reaction at the platinum surface. Catalysts that have accumulated too much coke may become unusable or must undergo a regeneration process.

Catalyst supports with a high surface area are typically desired because they allow a higher dispersion of platinum on the support surface. A high surface area generally corresponds to smaller pore diameters of the catalyst support. If the surface area is too high the pore diameters may be so small that they are prone to plugging from coke. This is because the smaller diameter pores are restricted so that oxygen used for regeneration cannot diffuse and reach the coke in the depths of the pores during the regeneration cycle. This ultimately leads to blocked pores containing platinum that is thus not accessible for the dehydrogenation reaction.

The present invention is therefore directed to a method of providing a dehydrogenation catalyst support and catalyst that overcomes these shortcomings.

SUMMARY

In an embodiment of the invention, a method of forming a dehydrogenation catalyst support is achieved by forming a mixture comprising a bayerite aluminum hydroxide (Al(OH)$_3$) and water into a support material. The support material is particulized. The particulized support material is compressed to a pressure of at least 5,000 psig to form a shaped body. The shaped body is calcined in pure steam at a temperature of at least 750° C. for at least 0.25 hours to form a catalyst support having an average pore diameter of 200 Å or greater.

In particular embodiments, the calcination is conducted at a temperature of from 750° C. to 1000° C. The calcination may be conducted from 2 hours to 10 hours at a temperature of from 750° C. to 1000° C.

In certain instances, the particulized support material may be compressed to a pressure of from 5,000 psig to 40,000 psig. In others, the particulized support material may be compressed to a pressure of from 14,500 psig to 15,500 psig. In still others, the particulized support material may be compressed to a pressure of from 5,000 psig to 40,000 psig with the calcination conducted in pure steam from 0.25 hours to 10 hours at a temperature of from 750° C. to 1000° C.

In another embodiment of the invention, a method of forming a dehydrogenation catalyst is carried out by forming a mixture comprising a bayerite aluminum hydroxide (Al(OH)$_3$) and water into a support material. The support material is particulized. The particulized support is compressed to a pressure of at least 5,000 psig for at least one second to form a shaped body. The shaped body is calcined in pure steam at a temperature of at least 750° C. for at least 0.25 hours to form a catalyst support having an average pore diameter of 200 Å or greater. The catalyst support is treated with a dehydrogenation catalyst component so that the catalyst support contains the dehydrogenation catalyst component to form the dehydrogenation catalyst.

In certain embodiments, the calcination is conducted at a temperature of from 750° C. to 1000° C. In others, the calcination is conducted from 0.25 hours to 10 hours at a temperature of from 750° C. to 1000° C.

In some instances, the particulized support material is compressed to a pressure of from 5,000 psig 40,000 psig. In others, the particulized support material is compressed to a pressure of from 14,500 psig to 15,500 psig, with the calcination being conducted in pure steam from 2 hours to 5 hours at a temperature of from 750° C. to 900° C.

In particular applications, the dehydrogenation catalyst component is comprised of at least one of platinum (Pt), tin (Sn), nickel (Ni), phosphorus (P), and calcium (Ca). In others, the dehydrogenation catalyst component is comprised of platinum (Pt), tin (Sn), nickel (Ni), phosphorus (P), and calcium (Ca).

In some embodiments, the catalyst contains platinum at a level of from 0.2 wt. % to 2 wt. %.

In certain instances, the dehydrogenation catalyst component is comprised of components (A)-(G), wherein:
(A) is platinum (Pt);
(B) is at least one of germanium (Ge), tin (Sn), lead (Pb), gallium (Ga), indium (In), and titanium (Ti);
(C) is at least one of iron, cobalt, nickel, and palladium;
(D) is phosphorus;
(E) is at least one of magnesium (Mg), calcium (Ca), strontium (Sr), barium (Ba), and a lanthanide;
(F) is chloride (Cl); and
(G) is manganese (Mn).

In certain instances, (A) may be platinum at a level of from 0.2 wt. % to 2 wt. %; (B) may be at least one of germanium, tin, lead, gallium, indium, and titanium, the total amount of component (B) being at a level of from 0.2 wt. % to 5 wt. %; (C) may be at least one of iron, cobalt, nickel, and palladium, the total amount of component (C) being at a level of from 0.2 wt. % to 5 wt. %; (D) may be phosphorus at a level of from 1 wt. % to 3 wt. %; (E) may be at least one of magnesium, calcium, strontium, barium, and a lanthanide, the total amount of component (E) being at a level of from 0.1 wt. % to 5 wt. %; (F) may be chloride at a level of 0.1 wt. % to 2 wt. %; and (G) may be manganese at a level of 0.05 wt. % to 5 wt. %.

In particular embodiments, (B) may be tin, (C) may be nickel, and (E) may be calcium.

In other instances, (A) may be platinum at a level of from 0.5 wt. % to 1.5 wt. %; the total amount of component (B) may be at a level of from 1 wt. % to 4 wt. %; the total amount of component (C) may be at a level of from 1 wt. % to 3 wt. %; (D) may be phosphorus at a level of from 1 wt. % to 3 wt. %; the total amount of component (E) may be at a level of from 1% to 5%; (F) may be chloride at a level of 0.15 wt. % to 1.0 wt. %; and (G) may be manganese at a level of from 0.1 wt. % to 2.5 wt. %.

In another aspect of the invention, a method of dehydrogenating hydrocarbons is carried out by contacting a hydrocarbon feed with a catalyst within a reactor in the presence of water vapor under dehydrogenation reaction conditions suitable to form dehydrogenated hydrocarbon products. The catalyst is that formed by a method wherein a mixture comprising a bayerite aluminum hydroxide ($Al(OH)_3$) and water are formed into a support material. The support material is particulized. The particulized support material is compressed to a pressure of at least 5,000 psig for at least 1 second to form a shaped body. The shaped body is calcined in pure steam at a temperature of at least 750° C. for at least 0.25 hours to form a catalyst support having an average pore diameter of 200 Å or greater. The catalyst support is treated with a dehydrogenation catalyst component so that the catalyst support contains the dehydrogenation catalyst component to form the dehydrogenation catalyst.

BRIEF DESCRIPTION OF THE DRAWINGS

For a more complete understanding of the present invention, and the advantages thereof, reference is now made to the following descriptions taken in conjunction with the accompanying figures, in which.

DETAILED DESCRIPTION

As used herein, "a" or "an" means one or more, with the singular encompassing the plural or the plural encompassing the singular unless expressly stated otherwise or is otherwise clear from the context. For example, the statement "contacting with a catalyst" should be understood to mean "contacting with one or more catalysts."

Furthermore, it should be understood that with respect to any concentration or amount range listed or described herein as being useful, suitable, or the like, it is intended to include every concentration or amount within the range, including the end points, and is to be considered as having been specifically stated. For example, "a range of from 1 to 10" is to be read as indicating each and every possible number along the continuum between about 1 and about 10. Thus, even if specific data points within the range, or even no data points within the range, are explicitly identified or refer to only a specific few, it is to be understood that the inventors appreciate and understand that any and all data points within the range are to be considered to have been specified, and that the inventors are in possession of the entire range and all points within the range.

A useful catalyst support and catalyst composition for the dehydrogenation of hydrocarbon compounds is provided by forming an alumina catalyst support under certain conditions to change the physical properties of the alumina support and also its surface chemistry by developing different alumina crystalline phases. For example, the alumina can be heated to change the crystalline structure from gamma to eta crystalline phase. In particular, the formed catalyst support has an average pore diameter of 200 Å (angstroms) or greater that results in high selectivity and conversion when used in dehydrogenation reactions, while providing excellent decoking properties. This results in higher conversions over time and a longer catalyst life.

Typically, catalyst supports for dehydrogenation of alkanes are inorganic oxides, and in most cases, the support is an alumina ($Al_2O_3$) support that is a crystalline alumina material, such as eta ($\eta$) alumina, theta ($\theta$) alumina, and gamma ($\gamma$) alumina crystalline materials.

In the present invention, the inorganic oxide forming the support is formed from a bayerite aluminum hydroxide (Al(OH)$_3$) support precursor that when processed under certain conditions results in a support where the primary component of the support is predominantly in the eta ($\eta$) and theta ($\theta$) alumina phases. In industrial practice, surface area values of alumina materials above 120 $m^2/g$ constituting eta ($\eta$) alumina phase and those under 120 $m^2/g$ constitute a theta ($\theta$) alumina phase. Bayerite is the required aluminum trihydroxide form because it gives the eta and theta crystalline form on calcination whereas the boehmite aluminum hydroxide does not.

In particular embodiments, the formed alumina catalyst support may be that having an average pore size ranging from 200 Å to 250 Å, and in other embodiments from 210 Å to 240 Å, and in still others from 220 Å to 230 Å.

The surface area of the formed alumina catalyst support may range from 60 $m^2/g$ to 100 $m^2/g$, and in others from 65 $m^2/g$ to 90 $m^2/g$, and in still others from 70 $m^2/g$ to 85 $m^2/g$.

The particle density refers to the particle density of the support particle not the intrinsic, skeletal or bulk density. The range of particle densities based on pore volume can vary from about 1.70 to 1.33 g/cc.

The catalyst support is formed by using certain preparation techniques involving calcination times and temperatures, calcination gas, compression pressures, and alumina structure modifiers. Boron is one modifier that was used in testing and it produced a support with the smallest pore diameters. This would normally be a good modifier to use in the cases where a small diameter is desirable, such as when using a platinum catalyst for hydrogenation of an alkene using hydrogen. In this case, however, where the production of propylene also produces coke, the small pores are a disadvantage because the pore openings become blocked by coke. Therefore, it was not desirable to use boron in making the support.

In preparing the catalyst support, the bayerite aluminum hydroxide support precursor material is mixed with a sufficient amount of water to make a paste, dough or other plastic mass. Rheology modifiers such as polyvinyl alcohol can be added to the alumina precursor paste to facilitate extrusion. Polyethylene glycol can be added to manipulate or facilitate pore formation. Lubricants such as stearic acid or graphite may be used during extrusion, as well as tableting. The formed support material is then dried.

The dried support material is then particulized by any method commonly known in the art, including, but not limited to, crushing, grinding, pulverizing, milling or otherwise forming into a powder. Particulizing (transforming into particles) can be performed by these and other methods and by combinations thereof. The particles or powder are then compressed, such as through tableting, wherein the particles or powder are subjected to compressive pressure to form the final shaped body forming the support. When tableting or compressing, the precursor material may be subjected to compressive pressure of from 5,000 psig to 40,000 psig or greater into a desired shape to form a shaped body. The compression may take place over a period of one second to 1 minute. In particular embodiments, the particles are compressed at a pressure of from 5,000 psig to 25,000 psig, more particularly from 14,500 psig to 20,000 psig. In specific embodiments, the particles may be compressed at a pressure of from 14,500 psig to 15,500 psig.

The final shaped body forming the support after compression and the resulting catalyst composition may be configured in various shapes and sizes. In one example, the shaped body for the support may be cylindrical in shape with a 1/8" diameter that may vary in length, such as 1/8" or less to up to several inches. In certain applications, the shape and size may be spherical or tablet-shaped or configured into other shapes, such as a star shape, with the thickness of the particle being of various thicknesses, which may be greater or less than 1/8" thick (e.g., 1/16" to 1/2").

The shaped body forming the catalyst support is then dried and calcined. Drying may be carried out at room temperature or an elevated temperature (e.g., from 100° C. to 140° C.). Drying facilitates giving the shaped body increased particle strength so that it will retain its shape during handling and when the calcination starts. Once the operating calcination temperature begins then steam is fed into the calciner over the catalyst support particles.

The calcination is carried out using steam ($H_2O$) as the calcination gas. The steam may be a pure steam or steam that is substantially air-free or free of nitrogen gas ($N_2$) and oxygen gas ($O_2$). The steam may have 1%, 0.5%, 0.25%, 0.1% or less by weight of any other gas other than $H_2O$. In forming the alumina catalyst support, particular calcination times and temperatures are used. In particular, the final calcination temperature will be a temperature of at least 750° C. wherein the shaped body is soaked in steam at that calcination temperature for at least 0.25 hours. In certain embodiments, the calcination may take place for at least 1 or 2 hours or more. As used herein, the expression "final calcination temperature" refers to the elevated temperature or temperatures of calcination required to complete the calcination. In particular embodiments, the final calcination temperature may range from 750° C. to 1000° C., with from 800° C. to 900° C. being particularly suitable.

The soak times at the final calcination temperature may vary depending upon the final calcination temperature. For example, at lower final calcination temperatures of around 750° C. to 850° C. the soak time in the air-free steam may range from 5 hours to 15 hours. At a final calcination temperature of from 850° C. to 900° C., the soak time in steam may range from 3 hours to 8 hours. At a final calcination temperature of from 900° C. to 950° C. the soak time in steam may range from 2 hours to 6 hours. At a final calcination temperature of from 950° C. to 1000° C. the soak time in steam may range from 1 hour to 5 hours.

In certain embodiments, a temperature ramp up during calcination with various soaking times in steam at different intervals may be used to perform the calcination of the shaped body to form the final catalyst support. Temperature ramp up rates of from 0.5° C. to 10° C./min may be used with periodic soak times in steam at various non-final calcination soak temperatures may range from 0 to 5 hours or more. An example of a suitable temperature ramp up and soak profile for the calcination of the catalyst support is provided in Table 1 below.

TABLE 1

| Ramp Temperature | Temperature Ramp Rate | Soak Time at Final Temp. |
| --- | --- | --- |
| 25-100° C. | 2-20° C./min (5° C./min preferred) | 0.5-5 hour (1 hour preferred) |
| 100-150° C. | 5° C./min | 1 hour |
| 150-340° C. | 10° C./min | 0 hour |
| 340-350° C. | 1° C./min | 1 hour |
| 350-490° C. | 10° C./min | 0 hour |
| 490-800° C. | 10° C./min | 5 hours |

After calcination, the calcined catalyst support is allowed to cool (e.g., room temperature).

The formed catalyst support may then be treated with a dehydrogenation catalyst component so that the final treated catalyst support contains the dehydrogenation catalyst component to form the final catalyst. The dehydrogenation catalyst component is meant to include those materials that are catalytically active, as well as those materials that may constitute promoters that promote the catalyst activity. This can include one or more different elements. Non-limiting examples of suitable dehydrogenation catalyst components that may be combined with the catalyst support include those described in U.S. Pat. No. 6,414,209 and U.S. patent application Ser. No. 13/742,439, filed Jan. 16, 2013, each of which is incorporated herein by reference in its entirety for all purposes.

In many embodiments, the dehydrogenation catalyst component includes platinum (Pt) and/or iridium (Ir) as an active catalyst component. Due to its availability, platinum may be used as the active catalyst component in many applications. The platinum may be combined with the catalyst support at a level of from 0.2% to 2% by weight of the catalyst. In particular embodiments, this component may be present in the catalyst composition at a level of from 0.5% to 1.5% by weight of the catalyst composition, and still more particularly from 0.7% to 1.2% by weight of the catalyst composition. Non-limiting examples of suitable sources of platinum that may be used in treating the catalyst support include chloroplatinic acid, platinous chloride and compounds containing the platinum amine complex. By way of clarification, unless stated otherwise or is otherwise apparent from its context, all percentage amounts are based on weight percentages of the catalyst composition (the support together with the added metal or elements forming the dehydrogenation catalyst components without any optional binder materials).

Iron (Fe), cobalt (Co), nickel (Ni), and palladium (Pd) may also be as a dehydrogenation catalyst component. These materials may be combined with the catalyst support so that they are present in the catalyst composition so that their combined or total amount is at a level of from 0.2% to 5% by weight of the catalyst. In other words, if only one of these elements is used, that element may be present at a level anywhere within that range. If more than one of these elements is used the sum of their amounts will fall within this range. In particular embodiments, these components may be present in the catalyst composition at a level of from 1% to 3% by weight of the catalyst composition.

In certain embodiments the dehydrogenation catalyst component is platinum only. In others, the dehydrogenation catalyst component may be platinum and tin only. In still others the dehydrogenation catalyst component may be palladium only, or nickel only.

In certain embodiments, lithium (Li), sodium (Na), potassium (K), rubidium (Rb), cesium (Cs), francium (Fr) are combined with the catalyst support as a catalyst component. These materials may be combined with the catalyst support so that they are present in the catalyst composition where the combined or total amount is at a level of from 0.1% to 5% by weight of the catalyst, more particularly from 0.5% to 3% by weight of the catalyst.

Phosphorus (P), which acts as a promoter, may also be combined with the catalyst support in forming the catalyst composition. The phosphorus may be present in the catalyst composition at a level of from 1% to 3% by weight of the catalyst composition. In particular embodiments, the phosphorus is present at a level of from 1.1% to 1.5% by weight of the catalyst composition. Examples of suitable sources of phosphorus used in treating the support in preparing the catalyst may include, but are not limited to, phosphonic, phosphinous, phosphorus, and phosphoric acids, salts and esters of such acids, and phosphorous halides. In particular, phosphoric acid ($H_3PO_4$) and ammonium hydrogen phosphate (($NH_4$)$_2$$HPO_4$) may be used as the phosphorus source. Other examples include hypophosphorous acid, phosphorous acid, peroxomonophosphoric acid, hypophosphoric acid, pyrophosphoric acid, triphosphoric acid, and the like, as well as combinations comprising at least one of the foregoing.

Various other materials may be combined with the catalyst support to form the catalyst composition. Such materials may include at least one element from the group consisting of germanium (Ge), tin (Sn), lead (Pb), gallium (Ga), indium (In), and titanium (Ti). These materials may be present in the catalyst composition so that their combined or total amount is at a level of from 0.2% to 5% by weight of the catalyst. In particular embodiments, these components may be present in the catalyst composition where their total is at a level of from 1% to 4% by weight of the catalyst composition, and still more particularly from 2% to 3.5% by weight of the catalyst composition. Sources of these materials that may be used in treating the catalyst support include their nitrates, hydroxides, halides, carbonates, acetates, and other water soluble salts so that they are present in the final catalyst. In particular embodiments tin is used in the catalyst composition.

The catalyst may further include at least one element from the group consisting of magnesium (Mg), calcium (Ca), strontium (Sr), barium (Ba), lanthanum (La), as well as the other lanthanides. These materials may be present in the catalyst composition so that their combined or total amount is at a level of from 0.1% to 5% by weight of the catalyst composition. In particular embodiments, these components may be present so that their total amount is at a level of from 1% to 3% by weight of the catalyst composition, and still more particularly from 1.2% to 2.0% by weight of the catalyst composition. In particular embodiments, calcium and barium may be used in the catalyst. Various sources of these materials may be used in treating the catalyst support so that they are present in the final catalyst.

The catalyst composition may also include chlorine (Cl). The chlorine may be present in the catalyst composition at a level of from 0.1% to 2% by weight of the catalyst composition. In particular embodiments, the chlorine may be present at a level of from 0.15% to 1% by weight of the catalyst composition, and still more particularly from 0.17% to 0.6% by weight of the catalyst composition. The chlorine may be provided by other components or their sources that are combined with or used in treating the catalyst support, such as chloride salts of the various components. In other cases, it may be provided by a separate chlorine source, such as hydrochloric acid (HCl), which is used to treat the support.

In certain applications, manganese (Mn) can be incorporated into dehydrogenation catalyst, as described in U.S. patent application Ser. No. 13/742,439. The manganese may be present in any amount, however, in certain embodiments it is present in the catalyst composition at a level of from 0.05% to 5% by weight of the catalyst. In other applications, the manganese may be present in the catalyst composition at a level from 0.1% to 2.5% by weight the catalyst. In particular embodiments, the manganese may be present at a level of from 0.1% to 1.0% by weight of the catalyst composition, and still more particularly from 0.2% to 0.3% by weight of the catalyst composition. Non-limiting examples of suitable sources of manganese include manganese oxides, as well as manganese nitrates, hydroxides, halides, carbonates, acetates, etc. Examples of manganese sources are also described in U.S. Pat. No. 4,547,618, which is incorporated herein by reference in its entirety for all purposes. Typically the manganese source is a manganese oxide or manganese carbonate, and is usually a salt that can be dissolved in water. These materials are applied to or otherwise combined with the catalyst support.

In forming the catalyst composition, the catalyst support is treated with the sources of the various materials described above. The various dehydrogenation catalyst components are typically dissolved in aqueous fluids that are then used to treat the catalyst support, such as through impregnation and incipient wetness, so that the catalyst support is impregnated with the solutions containing the dehydrogenation catalyst component(s).

In preparing the catalyst composition, a treatment solution may be made by adding the metal salts, phosphoric acid, chloride source (e.g., HCl), etc., and water together. The elements can be added to the mixture in various forms such as acids or metal salts and can be in the form of such as nitrates, ammonium, or chloride salts and can be hydrated salts. Carbonates such as calcium carbonate can also be used.

The pH of the catalytically active component can be adjusted by addition of an acid, such as hydrochloric acid, nitric acid, sulfuric acid, acetic acid, oxalic acid, and formic acid, or a base such as sodium hydroxide, ammonium hydroxide, potassium hydroxide, sodium (bi)carbonate, and potassium (bi)carbonate. An acidic pH range is used to prevent metal hydroxides from forming which could cause precipitation of the some of the metal species which may result in lower metal dispersion on the alumina surface and consequently lower catalyst performance.

The concentration of the catalytically active components in the impregnating solution can vary widely, for example from 0.01 to 10 molar or more, depending on the solubility of the particular materials employed. For example, the mixture can comprise: from 0.2% to 2% platinum, particularly from 0.5% to 1.5% platinum, and more particularly from 0.7% to 1.2% platinum; from 0.2% to 5% tin, particularly from 1% to 4% tin, and more particularly from 2% to 3.5% tin; from 0.1% to 4% nickel, particularly from 0.5% to 2.5% nickel, and more particularly from 0.8% to 1.5% nickel; from 0.1% to 5% calcium, particularly from 1% to 5% calcium, and more particularly from 1.2% to 2.0% calcium. The phosphorus component can be present in an amount of from 0.5% to 4%, particularly from 0.7% to 3%, and more particularly from 0.8% to 1.5%, all percentages based upon a total weight of the mixture.

The treatment solution may then be added all at once to the catalyst support, which is then mixed until the solution is adequately absorbed into the support. In certain instances, the impregnation solution may be applied to the catalyst within one hour after the solution is made, preferably within 45 minutes and even less than 20 minutes. The solution may be constantly agitated. The support can be immersed in the impregnating solution for a period of time sufficient to impregnate the support. The impregnation time can be, for example, up to 10 hours, e.g., 0.5 to 10 hours, and can occur at room temperature. The support can be immersed in the impregnating solution, with or without agitation (e.g., stirring) for all or for a portion of the impregnation period. The wet alumina support may then be dried prior to calcining (e.g., 120° C. in air for one or more hours). The drying can occur at room temperature or at an elevated temperature of 25° C. to 500° C., more particularly from 120° C. to 200° C., for a period of time sufficient to dry the impregnated support. The drying time can be 0.5 to 10 hours, particularly 0.5 to 5 hours. The dried catalyst particle may then be calcined in air, nitrogen, or other gas. The calcining can occur at a temperature of from 200° C. to 1,000° C., particularly from 500° C. to 800° C., more particularly from 550° C. to 700° C., for a period of time sufficient for calcination. The calcination can be for 1 to 20 hours, particularly 5 to 15 hours, and more particularly 8 to 12 hours. The calcination can occur at various temperatures for different amounts of time. Any commercial calciner can be used, such as fixed bed or rotating calciners. Calcination can be performed in various atmospheres such as in air, oxygen, inert atmosphere (e.g., nitrogen), steam, or mixtures thereof. The total preparation time of the catalyst can be, for example, 1 to 40 hours.

The calcining may include ramping the temperature in various stages. An example of a typical calcination profile includes increasing the catalyst bed temperature at 5° C./minute to 100° C. and soaking in air for 5 hours; increasing the catalyst bed temperature at 5° C./minute to 150° C. and soaking in air for 5 hours; increasing the catalyst bed temperature at 5° C./minute to 340° C.; increasing the catalyst bed temperature at 1° C./minute to 350° C. and soaking in air for 2 hours; increasing the catalyst bed temperature at 10° C./minute to 540° C.; increasing the catalyst bed temperature at 1° C./minute to 550° C. and soaking in air for 2 hours. Once calcined, the catalyst is cooled to room temperature.

The substrate or final catalyst composition may be configured in various shapes and sizes. In one example, the shape and size may be cylindrical in shape with a ⅛" diameter that may vary in length, such as ⅛" or less to up to several inches. In certain applications, the shape and size may be spherical or tablet-shaped or configured into other shapes, such as a star shape, with the thickness of the particle being of various thicknesses, which may be greater or less than ⅛" thick (e.g., 1/16" to ½"). The substrate may be calcined prior to incorporation of the other components to ensure it has the proper surface area and pore structure and crystalline phase. Once calcined, the substrate is impregnated with the metals solution. The non-impregnated substrate can be dried (e.g., 120° C. for 2 hours) before the impregnation if desired.

The formed catalyst composition may be used in hydrocarbon conversion reactions, particularly in dehydrogenation reactions. In particular, the catalyst composition may be used in the dehydrogenation of those paraffins or alkane hydrocarbons of from $C_2$ to $C_{20}$, more particularly, those hydrocarbons of from $C_2$ to $C_5$, and still more particularly those from $C_3$ to $C_4$. The catalyst composition has particular application in the conversion of propane to propylene.

In use, the catalyst may be used in a reactor and contacted with a hydrocarbon feed that is introduced in the reactor under hydrocarbon conversion conditions to form hydrocarbon conversion products. The hydrocarbon feed may be a paraffin or alkane hydrocarbon feed and the conversion conditions may be those dehydrogenation reaction conditions useful to form dehydrogenated hydrocarbon products, such as a propane feed that is dehydrogenated to form propylene.

A steam or water co-feed is typically used in the reaction with the hydrocarbon feed. The steam or water may act as a carrier gas to facilitate introduction of the hydrocarbon into the reactor. The purpose of using steam is to carry heat into the reactor since the dehydrogenation is an endothermic reaction. Steam also helps to minimize coke formation. Steam is known to at least partially remove or inhibit coke formation on the catalyst. The steam also serves to dilute the hydrocarbon feed so the catalyst is not quickly coked and the reactor is not cooled too much due to the endothermic dehydrogenation reaction. Steam also serves as a diluent that shifts the equilibrium conversion to higher values. In certain applications, the hydrocarbon/$H_2O$ molar feed ratio may range from 1:1 to 10:1, more particularly from 1:2 to 1:6. A hydrocarbon/water molar feed of 1:3 to 1:5 has been found particularly useful for the dehydrogenation of propane.

The dehydrogenation reaction may be a non-oxidative dehydrogenation reaction wherein the reaction is carried out in an oxygen-free or substantially oxygen-free (i.e., no oxygen gas or $O_2$) environment. Furthermore, the reaction may be carried out without any hydrogen gas ($H_2$) co-feed, as is used in some dehydrogenation reactions. Diluents, which may be inert diluents, such as helium or nitrogen, may also be used in the reaction.

The feed streams may be preheated and introduced into the dehydrogenation reactor at temperatures that may range from 200° C. to 700° C. The hydrocarbon, steam and diluent feed may be introduced into the reactor at a GHSV of from 2100 $hr^{-1}$ to 4500 $hr^{-1}$, more particularly from 3000 $hf^{-1}$ to 3500 $hr^{-1}$.

Because the dehydrogenation reaction is endothermic, heat input is typically required to maintain the reaction. The dehydrogenation reaction may be carried out in a tube-type fixed bed reactor that is provided with a heat source to maintain suitable reaction temperatures. Other suitable reactors may be used however. The reaction temperatures are typically maintained at from 525° C. to 650° C., more particularly from 545° C. to 595° C.

After a period of use, the catalyst may be regenerated to remove coke buildup. In a typical regeneration cycle after dehydrogenation, an inert purge of the catalyst bed with $N_2$ is followed by the addition of dilute air (1-20 volume % $O_2$) to oxidize coke to either carbon monoxide or carbon dioxide for a specified period of time. Addition of steam during this period is optional. Once the regeneration or oxidation of coke is stopped an inert purge with $N_2$ is started again before starting the next dehydrogenation period. The time scales of $N_2$ purge and regeneration could vary anywhere from 10-180 minutes. In addition the temperatures during regeneration may be reduced to accommodate the temperature raise due to exothermic oxidation during the regeneration.

Because of the pore configuration and larger pore size of the catalyst support, the catalyst composition has been found to provide high conversion and selectivity when used in dehydrogenation reactions, while providing increased decoking during regeneration cycles, which increases catalyst life. The catalyst composition has been found to be particularly useful in propane dehydrogenation. The extended life of the catalyst reduces overall catalyst and product costs.

The following examples better serve to illustrate the invention.

EXAMPLES

Example 1

Various catalyst supports (Samples A-G) were prepared using different preparation techniques with different compression pressures, calcination temperatures, and calcination gases. For each support, a bayerite aluminum hydroxide (Al(OH)$_3$) powder was mixed with a sufficient amount of deionized water to form a paste that was then used to form the Samples A-G.

With respect to Sample G, boron (B) as boric acid was also mixed with the bayerite aluminum hydroxide and water in an amount to provide 0.1 mole % boron by total moles of boron oxide and alumina of the final support. The paste in each sample was dried and powdered to make a tablet. After tableting, the tablet was dried and calcined in different calcination gases at various temperatures for a soak time of 5 hours in the calcination gas at the final calcination temperature. The following Table 2 lists the different conditions used in forming each of the samples.

TABLE 2

| Sample | Calcination Gas | Tableting Pressure (psi) | Calcination Temp. (°C.) |
|---|---|---|---|
| A | Steam | 15,000 | 800 |
| B | Air | 15,000 | 900 |
| C | $N_2$ | 15,000 | 900 |
| D | Air | 15,000 | 800 |
| Comparative Sample | | | |
| E | $N_2$ | 10,000 | 800 |
| F | $N_2$ | 15,000 | 800 |
| G | $N_2$ | 15,000 | 800 |

With respect to Samples A, B, C and D, the preparation was similar to Comparative Samples E and F except steam was used in Sample A by pumping 0.001 mL of liquid water into the furnace where it was immediately vaporized into steam. The steam was flowed during the calcination period at 800° C.

Samples B and D were prepared similarly to Samples E and F except that air was flowed into the calcination tube furnace over the alumina precursor sample at 100 mL/min during the calcination at 900° C.

Sample C was prepared similar to Samples E and F except nitrogen gas was fed into the calcination tube furnace and was flowed over the samples at 100 mL/min using a calcination temperature of 900° C.

With respect to Comparative Sample F, bayerite and boric acid were mixed with water and made into a paste. The paste was dried in air at 240° C. for 3 hours, then ground into a powder, pressed at 15 k psig into a tablet with a top and bottom surface area each equal to 25.4 square millimeters (one square inch) by 1 to 10 mm thickness using a Carver press, sized to −20 mesh to +40 mesh and calcined at 800° C. from 1 to 5 hrs in a 1 inch diameter tube furnace. Nitrogen gas was passed over the alumina support at about 100 mL/min during calcination. With respect to Comparative Sample E, the preparation was the same as that for Comparative Sample F except 10,000 psig was used to press the alumina precursor tablet.

With respect to the preparation of Comparative Sample G, bayerite and boric acid were mixed with water and made into a paste. The paste was dried in air at 240° C. for 3 hours, then ground into a powder, pressed at 15,000 psig into a tablet with a top and bottom surface area each equal to 6.45 square centimeters (one square inch) by 1 to 10 mm thickness using a Carver press, sized to −20 mesh to +40 mesh and calcined at 800° C. from 1 to 5 hrs in a 1 inch (2.54 cm) diameter tube furnace. Nitrogen gas was passed over the alumina support at about 100 mL/min during calcination. In an alternate preparation the bayerite was physically mixed by hand or by mechanical blender with boric acid (dry), the mixture was pressed at 15,000 psig, sized, and then calcined at 800° C. In yet another alternate preparation the bayerite was pressed at 15,000 psig to form a tablet as described above, calcined at 800° C., then boric acid and water were added to the tablet and dried for 3 hours at 240° C. in air.

The pore diameter and surface areas of each of all samples were measured using the Nitrogen B.E.T. analytical technique. The results are presented in Table 3 below.

TABLE 3

| Sample | BET Surface Area ($m^2$/g) | Total Pore Volume (cc/g) | Average Pore Diameter (Å) |
|---|---|---|---|
| A | 122 | 0.4402 | 145 |
| B | 84 | 0.4671 | 224 |
| C | 78 | 0.453 | 231 |
| D | 168 | 0.501 | 119 |
| E | 156 | 0.4393 | 113 |
| F | 137 | 0.4634 | 136 |
| G | 146 | 0.435 | 119 |

Figure 1:
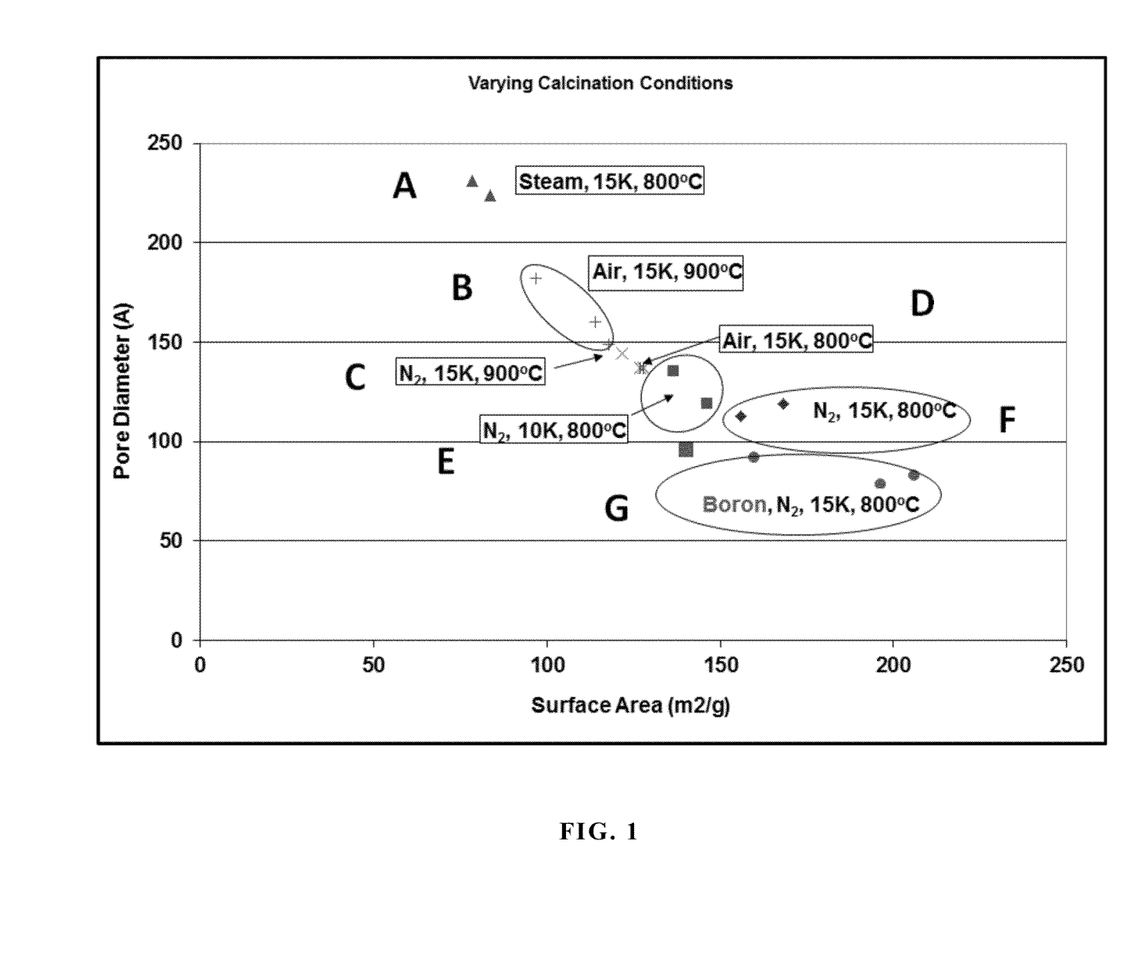
FIG. 1 is a plot of the average pore diameter versus surface area for several alumina catalyst supports prepared using different methods.

FIG. 1 shows the plot of pore diameter in angstroms (Å) versus the surface area for each support sample. Additionally, FIG. 1 shows the plot of pore diameter and surface area for a commercial off the shelf eta-alumina support, which is indicated by the large square at about 96 Å pore diameter. All of the Samples A-G were generated using bayerite or aluminum trihydroxide, which is a versatile alumina precursor that can give the eta/theta crystalline form. These crystalline forms cannot be obtained with a boehmite alumina precursor generally used in manufacture of alumina supports. Unexpectedly, it was determined that having oxygen as oxygen gas $O_2$ or as $H_2O$ in the calcination gas aids in increasing the pore diameter and lowering the surface area of the alumina catalyst support. In addition, the conditions necessary to produce the eta and theta forms of alumina by a combination of time and temperature were determined. Eta alumina is defined as an alumina originating from a bayerite precursor calcined to obtain an alumina with greater than 120 $m^2$/g surface area.

Figure 2:
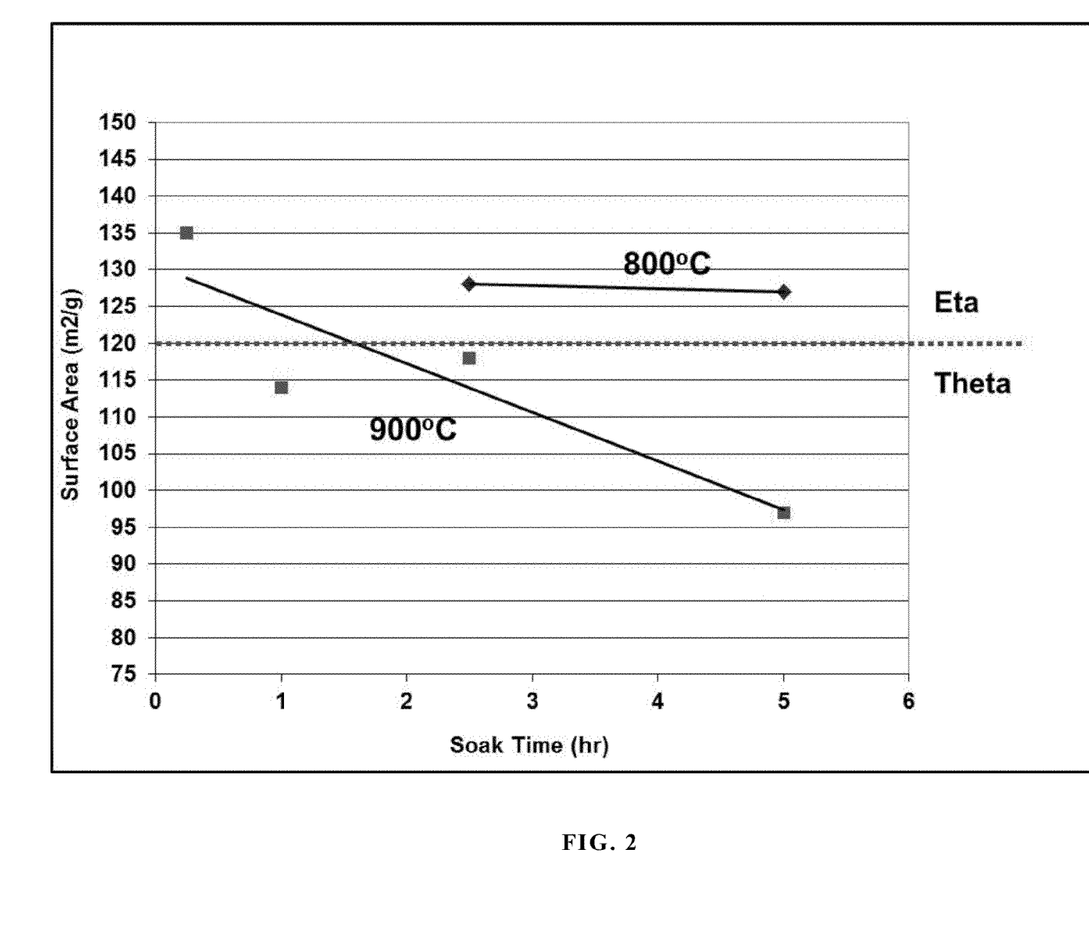
FIG. 2 is a plot of alumina surface area versus calcination soak time leading to eta and theta crystalline phases.

Referring to FIG. 2, at 800° C. it requires a substantially long period of calcination time to produce the theta form of alumina if desired. The calcination time can be significantly shortened by increasing the temperature to 900° C. This understanding is necessary to be able to adjust the surface area and pore volume properties shown in FIG. 1.

Example 2

Support Samples A, E, F, and G from Example 1 were used to form Catalysts A, E, F, and G, respectively, with Catalysts E, F and G constituting comparative catalysts. Each of the supports was treated to provide the dehydrogenation catalyst components Pt, Sn, Ni, P, Ca, and Cl on the support in the same amounts using the treatment procedures outlined in the detailed description to form dehydrogenation catalysts, Catalyst A and Comparative Catalysts E, F and G. The following recipe of Table 4 was used to impregnate the supports:

TABLE 4

| 1% P; Ca:Ni:P = 0.9:0.1:1 | Required | |
|---|---|---|
| Order of addition | g | mL |
| $H_3PO_4$ | 0.3 | 0.179 |
| HCl (conc) | 0.08 | 0.07 |
| Water | 1.41 | 1.41 |
| $Ni(NO_3)_2 \cdot 6H_2O$ | 0.073 | |
| $SnCl_2 \cdot 2H_2O$ | 0.22 | |
| $Ca(NO_3)_2 \cdot 4H_2O$ | 0.56 | |
| $H_2PtCl_6$, aq, 20% Pt | 0.21 | 0.18 |
| Support | 5 | |
| 800° C., 100% $N_2$, 5 hrs | | |

The catalysts had average metal concentrations of 0.72 wt % Pt, 2.55 wt % Sn, 0.28 wt % Ni, 1.17 wt % P, 1.50 wt % Ca, and 0.27 wt % Cl.

Each of the catalysts was then used in the dehydrogenation of propane to form propylene at the same catalyst loading and at the same conversion level and process conditions at 595° C. The conversion, selectivity and time on stream are presented in FIG. 3, along with the plots for pore diameter and surface area from FIG. 1 for each support of Catalysts A, E, F, and G.

Figure 3:
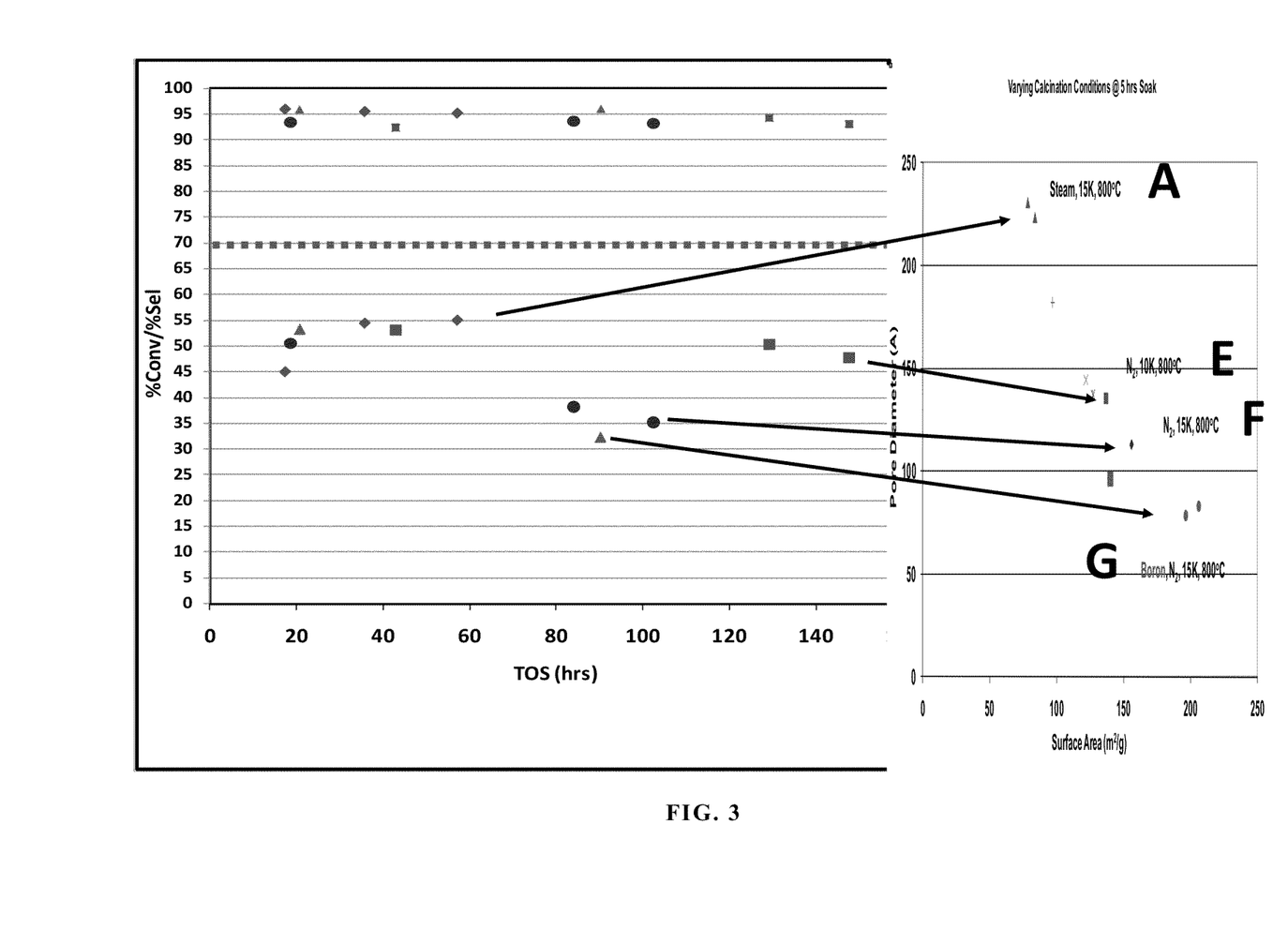
FIG. 3 is a plot of conversion, selectivity and time on stream using different supports and their effectiveness over time after regeneration.

Each data point of FIG. 3 represents a cycle of use, wherein the catalysts were used in the dehydrogenation reaction and then regenerated before being used again. A typical regeneration cycle after dehydrogenation involved an inert purge with $N_2$ followed by dilute air (1-20 volume % $O_2$) addition to oxidize coke to either carbon monoxide or carbon dioxide for a specified period of time. Addition of steam during this period was optional. Once the regeneration or oxidation of coke was stopped, an inert purge with $N_2$ was started again before starting the next dehydrogenation period. The time scales of $N_2$ purge and regeneration could vary anywhere from 10-180 minutes. In addition, the temperatures during regeneration were reduced as necessary to accommodate the temperature raise due to exothermic oxidation during the regeneration.

The horizontal demarcation line in FIG. 3 at about 70% indicates the theoretical maximum conversion. The data points below this line indicate the conversion for each catalyst, while the date points above this line indicate catalyst selectivity.

As can be seen from FIG. 3, Catalyst A, which was formed at 15,000 psig and calcined at 800° C. in steam, showed the best performance. A lower curve slope between the data points for each catalyst indicates the catalyst was being decoked more efficiently. A downward trend indicates that not all of the coke was being removed during regeneration and so each subsequent dehydrogenation cycle in the conversion was lower. For Catalyst A, the conversion was approximately 55%. It is evident that although Catalyst A and Comparative Catalysts E, F and G started high in conversion, reaching a maximum conversion of 50-55%, the Comparative Sample Catalysts E, F, and G drop off in activity, as evidenced by declining conversion curves over time on stream (TOS) very quickly. The Catalyst A showed no drop off in conversion after each subsequent regeneration. The behavior of these catalysts shows very clearly that the higher the pore diameter the more effective the regeneration by more effectively removing the coke. Since the coke is effectively removed with each regeneration in Catalyst A then the platinum is available for dehydrogenation and the propane to propylene conversion stays high without decline.

While the invention has been shown in only some of its forms, it should be apparent to those skilled in the art that it is not so limited, but is susceptible to various changes and modifications without departing from the scope of the invention. Accordingly, it is appropriate that the appended claims be construed broadly and in a manner consistent with the scope of the invention.

We claim:

1. A method of forming a dehydrogenation catalyst support comprising:
   forming a mixture comprising a bayerite aluminum hydroxide ($Al(OH)_3$) and water into a support material;
   particulizing the support material;
   compressing the particulized support material to a pressure of at least 5,000 psig to form a shaped body; and
   calcining the shaped body in pure steam at a temperature of at least 750° C. for at least 0.25 hours to form a catalyst support having an average pore diameter of 200 Å or greater.

2. The method of claim 1, wherein:
   the calcination is conducted at a temperature of from 750° C. to 1000° C.

3. The method of claim 1, wherein:
   the calcination is conducted from 2 hours to 10 hours at a temperature of from 750° C. to 1000° C.

4. The method of claim 1, wherein:
   the particulized support material is compressed to a pressure of from 5,000 psig to 40,000 psig.

5. The method of claim 1, wherein:
   the particulized support material is compressed to a pressure of from 14,500 psig to 15,500 psig; and wherein the calcination is conducted in pure steam from 0.25 hours to 10 hours at a temperature of from 750° C. to 1000° C.

6. A method of forming a dehydrogenation catalyst comprising:
   forming a mixture comprising a bayerite aluminum hydroxide ($Al(OH)_3$) and water into a support material;
   particulizing the support material
   compressing the particulized support material to a pressure of at least 5,000 psig for at least one second to form a shaped body;
   calcining the shaped body in pure steam at a temperature of at least 750° C. for at least 0.25 hours to form a catalyst support having an average pore diameter of 200 Å or greater; and
   treating the catalyst support with a dehydrogenation catalyst component so that the catalyst support contains the dehydrogenation catalyst component to form the dehydrogenation catalyst.

7. The method of claim 6, wherein:
   the calcination is conducted at a temperature of from 750° C. to 1000° C.

8. The method of claim 6, wherein:
   the calcination is conducted from 0.25 hours to 10 hours at a temperature of from 750° C. to 1000° C.

9. The method of claim 6, wherein:
   the particulized support material is compressed to a pressure of from 5,000 psig 40,000 psig.

10. The method of claim 6, wherein:
    the particulized support material is compressed to a pressure of from 14,500 psig to 15,500 psig; and wherein the calcination is conducted in pure steam from 2 hours to 5 hours at a temperature of from 750° C. to 900° C.

11. The method of claim 6, wherein:
    the dehydrogenation catalyst component is comprised of at least one of platinum (Pt), tin (Sn), nickel (Ni), phosphorus (P), and calcium (Ca).

12. The method of claim 11, wherein:
    the catalyst contains platinum at a level of from 0.2 wt. % to 2 wt. %.

13. The method of claim 6, wherein:
    the dehydrogenation catalyst component is comprised of platinum (Pt), tin (Sn), nickel (Ni), phosphorus (P), and calcium (Ca).

14. The method of claim 6, wherein:
    the dehydrogenation catalyst component further comprises components (A) - (G), wherein:
    (A) is platinum (Pt);
    (B) is at least one of germanium (Ge), tin (Sn), lead (Pb), gallium (Ga), indium (In), and titanium (Ti);
    (C) is at least one of iron, cobalt, nickel, and palladium;
    (D) is phosphorus;
    (E) is at least one of magnesium (Mg), calcium (Ca), strontium (Sr), barium (Ba), and a lanthanide; and
    (F) is chloride (Cl); and
    (G) is manganese (Mn).

15. The method of claim 14, wherein:
    (A) is platinum at a level of from 0.2 wt. % to 2 wt. %;

(B) is at least one of germanium, tin, lead, gallium, indium, and titanium, the total amount of component (B) being at a level of from 0.2 wt. % to 5 wt. %;

(C) is at least one of iron, cobalt, nickel, and palladium, the total amount of component (C) being at a level of from 0.2 wt. % to 5 wt. %;

(D) is phosphorus at a level of from 1 wt. % to 3 wt. %;

(E) is at least one of magnesium, calcium, strontium, barium, and a lanthanide, the total amount of component (E) being at a level of from 0.1 wt. % to 5 wt. %;

(F) is chloride at a level of 0.1 wt. % to 2 wt. %; and (G) is manganese at a level of 0.05 wt. % to 5 wt. %.

16. The method of claim 14, wherein:

(B) is tin, (C) is nickel, and (E) is calcium.

17. The method of claim 14, wherein:

(A) is platinum at a level of from 0.5 wt. % to 1.5 wt. %;

the total amount of component (B) is at a level of from 1 wt. % to 4 wt. %;

the total amount of component (C) is at a level of from 1 wt. % to 3 wt. %;

(D) is phosphorus at a level of from 1 wt. % to 3 wt. %;

the total amount of component (E) is at a level of from 1 % to 5 %;

(F) is chloride at a level of 0.15 wt. % to 1.0 wt. %; and (G) is manganese at a level of from 0.1 wt. % to 2.5 wt. %.

18. A method of dehydrogenating hydrocarbons comprising:

contacting a hydrocarbon feed with a catalyst within a reactor in the presence of water vapor under dehydrogenation reaction conditions suitable to form dehydrogenated hydrocarbon products, the catalyst being that formed by a method comprising:

forming a mixture comprising a bayerite aluminum hydroxide ($Al(OH)_3$) and water into a support material;

particulizing the support material;

compressing the particulized support material to a pressure of at least 5,000 psig for at least 1 second to form a shaped body;

calcining the shaped body in pure steam at a temperature of at least 750° C. for at least 0.25 hours to form a catalyst support having an average pore diameter of 200 Å or greater; and treating the catalyst support with a dehydrogenation catalyst component so that the catalyst support contains the dehydrogenation catalyst component to form the dehydrogenation catalyst.

* * * * *